United States Patent [19] [11] Patent Number: 5,049,503
Swanson et al. [45] Date of Patent: Sep. 17, 1991

[54] METHOD FOR AFFECTING FERTILITY IN PLANT VARIANTS

[75] Inventors: Eric B. Swanson, Guelph; Marc P. Coumans, Georgetown, both of Canada

[73] Assignee: Pioneer Hi-Bred International, DesMoines, Iowa

[21] Appl. No.: 470,449

[22] Filed: Jan. 18, 1990

Related U.S. Application Data

[63] Continuation of Ser. No. 119,452, Nov. 18, 1987, abandoned.

[51] Int. Cl.$^5$ ............................ C12N 5/04; A01H 4/00
[52] U.S. Cl. ................................ 435/240.4; 800/200; 800/230; 800/DIG. 15
[58] Field of Search ............ 435/240.4, 240.5, 240.51; 800/230, DIG. 15, DIG. 16, 17, 200

[56] References Cited

PUBLICATIONS

Karp, "Can Genetic Instability be Controlled in Plant Tissue Cultures?" IAPTC #57, Mar. 89.
Morrison et al., "Haploid Plants From Tissue Culture: New Plant Varieties in a Shortened Time Frame", Bio/Technology, vol. 6, Jun. 1988.
Henry et al., Theor. Appl. Genet. 67: 439–42 (1984).
Datta & Wenzel, Plant Sci. 48: 49–54 (1987) "Isolated Microspore Derived Plant Formation Via Embryogenesis . . . ".
Stringam (1979) Regenertion in . . . Z. Pflanzenphysiol. Bd. 92. S. 459–462.
Larkin, et al., (1981) Somaclonal Variation . . . Theor. Appl. Venet. 60: 197–214.
Swanson, et al., 91987) Efficient Isolation of . . . Plant Cell Reports 6: 94–97.
Chuong, et al., (1985) High Frequency Embryogenesis . . . Plant Science 39: 219–226.
Tyrnov in Apomixis and Breeding S. S. Khokhlov, ed. Amerind Publishing Co. Pvt. Ltd., New Delhi 1976 p. 278 Todua, et al., ibid p. 304.
Pirrie, et al., The Production of Fertile, Triploid . . . Theor. Appl. Genet. (1986) 72, 48–52.
Hoffmann, et al., Anther Culture as a Breeding . . . Theor. Appl. Genet. 61: 225–232 (1982).
Chaleff (1983) Science 219: 676–682.
Gengenbach et al., (Mar. 1982) Maize Benefits Cooperation News Letter 56: 140–142.
Brettell (1980) Theor. Appl. Genet. 58: 55–58.
Hoffmann et al., (1982) Theor. Appl. Genet. 61: 225–232.

*Primary Examiner*—Elizabeth C. Weimar
*Assistant Examiner*—Che S. Chereskin
*Attorney, Agent, or Firm*—Foley & Lardner

[57] ABSTRACT

Plant embryogenesis from cultured, immature gametic cells can be exploited to overcome the problem of phenotypic sterility in the products of many techniques for plant modification, including interspecific and intergeneric sexual crossing or somatic fusion somaclonal selection, genetic transformation and mutagenesis.

13 Claims, No Drawings

METHOD FOR AFFECTING FERTILITY IN PLANT VARIANTS

This is a continuation of application Ser. No. 07/119,452 filed Nov. 20, 1987, abandoned.

BACKGROUND OF THE INVENTION

The present invention relates to a system, based on the use of immature gametic cells, for influencing the fertility of plant material that is phenotypically sterile by virtue of a manipulation such as interspecific or intergeneric sexual hybridization or somatic fusion, somaclonal selection, genetic transformation or mutagenesis.

As advances are made in different methods for producing useful variants from existing plant material, it has become evident that the effective sterility which is characteristic of many such variants presents a major hurdle to their widespread use in breeding programs. It is well known, for example, that sexual crossability between phylogenetically distant plant types is generally limited by incompatibility resulting from disturbed pollen/stigma and pollen-tube/style interactions, from failure of zygote development, and from embryo or endosperm disruption.

Although embryo rescue may permit one to obtain variants from an interspecific or intergeneric sexual crossing, such variants are nearly always virtually sterile. For example, Mohapatra and Bajaj, *Euphytica* 36: 321-26 (1987), attempted the interspecific hybridization via embryo rescue of an oil-yielding Brassica species, *B. juncea*, with white mustard (*B. hirta*), which is resistant to leaf blight, but the $F_1$ plants displayed large morphological diversity, including abnormal, aneuploid and sterile flowers, and markedly reduced fertility.

There are also numerous reports in the literature that concern the sterility or near-sterility of many somatic hybrids. A frequent result of protoplast fusions aimed at producing interspecific and intergeneric hybrids has been the development of sterile or near-sterile plants. Thus, Hoffman and Adaihi, *Planta* 153: 586-93 (1981) describe a sterile intergeneric somatic hybrid produced by fusion of Arabidopsis sp. and Brassica sp. protoplasts. In *IAPTC Newsletter,* No. 38 (October, 1982), at pages 6-12, Harms et al attribute results such as these to various mechanisms of somatic incompatibility, including chromosome rearrangement, nuclear-cytoplasmic interaction and interorganelle competition.

By the same token, the production of transgenic plants, for example, by Agrobacterium-mediated transformation or direct DNA transfer, can be accompanied by modifications of the donor DNA (deletions, partial duplications, point mutations). See Czernilofsky et al, *DNA* 5: 473-82 (1986). Modifications of this sort may explain the high incidence of sterility among transgenic plants, for example, as reported by Chyi et al, *Mol. Gen. Genet.* 204: 64-69 (1986). Sterility problems are also prevalent in applications of culturing techniques to exploit mutational and somaclonal variation. Thus, Evans and Sharp, *Bio/Technology* 4: 528-32 (1986), and D'Amato, *CRC Critical Rev. Plant Sci.* 3: 73-112 (1985), note the widespread incidence of altered chromosome number and other chromosomal aberrations among variant plants regenerated from cell culture.

The conventional approach to overcoming phenotypic sterility in plant variants has been to attempt a sexual cross between the variant and another plant that may provide a fertility-restoring genetic contribution to some of the progeny. This approach is limited by its requirement that there be no intractable sexual-incompatibility barriers to the proposed cross, and that the progeny of the cross are viable. The conventional approach is also limited to the extent that the contemplated sexual cross employs pollen from the variant, even when production of normal pollen by the variant may be only a fraction of normal levels. Moreover, use of pollen from the variant means that the latter's cytoplasmic traits, which are in general inherited solely maternally, will probably be lost to any fertile progeny.

SUMMARY OF THE INVENTION

It is therefore an object of the present invention to provide a method for imparting fertility to phenotypically-sterile plant material, which method does not rely on sexual crossing.

It is also an object of the present invention to provide a process for the rapid fixation of a trait, even a recessive trait, when the genetic determinant for that trait is introduced into one plant species from another, dissimilar species.

It is a further object of the present invention to provide fertile plants that possess one or more desirable traits characterizing phenotypically-sterile variant material from which the plants were derived.

In accomplishing the foregoing objects, there has been provided, in accordance with one aspect of the present invention, a process for affecting plant fertility, comprising the steps of (A) producing a culture of immature gametic cells obtained from a donor plant that is phenotypically sterile, (B) generating a plurality of plant embryos from cells in the culture, and (C) determining which embryos in the plurality are developable into fertile plants. In one preferred embodiment, the immature gametic cells are microspores which are obtained, for example, from a Brassica donor plant or other crop providing regenerable microspores. In other preferred embodiments, the phenotypically-sterile donor plant is a somatic hybrid, the product of an interspecific or intergeneric sexual cross, a transgenic plant, or a variant isolated from cell culture.

In accordance with another aspect of the present invention, a plant has been provided that is the product of a process as described above, which plant is fertile but otherwise displays one or more identifying characteristics of the phenotypically-sterile donor plant. In one preferred embodiment, the fertile plant is a *Brassica napus* plant characterized by (i) parental-type acetolactate synthase (ALS), i.e., by an enzymatic activity similar to that of a parent of the donor plant, and (ii) a resistance to chlorsulfuron, a sulfonylurea herbicide which binds ALS. In another preferred embodiment, the fertile plant is a *Brassica napus* plant produced using immature gametic cells from a donor plant that is a somatic hybrid, which immature gametic cells are exposed to a host-specific toxin produced by *Alternaria brassicae* during the above-described process.

Other objects, features and advantages of the present invention will become apparent from the following detailed description. It should be understood, however, that the detailed description and the specific examples, while indicating preferred embodiments of the invention, are given by way of illustration only, since various changes and modifications within the spirit and scope of the invention will become apparent to those skilled in the art from this detailed description.

DETAILED DESCRIPTION OF PREFERRED EMBODIMENTS

It has been discovered that the problem of sterile (or virtually sterile) phenotypes among the products of many plant-modification techniques, including interspecific or intergeneric sexual and somatic hybridization, the use of mutagenic agents, somaclonal selection and genetic transformation, can be overcome by incorporating into any such technique the step of producing embryos from immature gametic cells of a phenotypically-sterile donor plant. In particular, the population of immature gametic cells from the functionally sterile parent can be tapped, pursuant to the present invention, as a ready source for meiotic recombination and segregation events that are realized thereafter in the form of regenerated plants which are fertile but which otherwise resemble (i.e., display one or more identifying characteristics of) the donor plant.

For purposes of the present description, the phrases "phenotypically sterile" and "functionally sterile" are used interchangeably with reference to a plant characterized by a level of fertility that is sufficiently low, compared to what is considered normal fertility for the species or line of which the plant is a member, to render the plant unusable in practice as a source for germplasm. One indicator of phenotypic sterility is seed set relative to the "wild type" of the pertinent species or line. In a given instance, a seed yield that is less than 50% of the average for the line from which a variant was derived could be deemed indicative of functional sterility; for another line, the threshold indication of phenotypic sterility could be lower, for example, 10% or 1% of average, or even lower.

Another indicator of functional sterility is the continued production of a high percentage of abortive (nonfunctional) pollen when variant plant material is used in a large number of outcrosses. What is "large" in this context would depend, again, on what is considered normal, in the context of pollen output, for the species or line representing the wild type of the variant in question. In general, the incidence among all pollen produced of only between about 1% to 10% functional pollen grains will be deemed indicative of phenotypic sterility; certainly, an output of functional pollen that is less than about 1% of the total would, in most varieties, qualify a plant as phenotypically sterile. (In this regard, "functional" pollen is pollen that will fertilize an egg cell and produce a viable embryo when the pollen is used in a cross under conditions that are normal for the species involved.) Similarly, a level of self-fertility that is less than 1% of what is expected in a normally self-fertilizing variety can serve as an indication that a variant plant derived from that variety is functionally sterile.

In accordance with the present invention, a suitable donor plant, though functionally sterile, must provide immature gametic cells that are amenable to culturing and regeneration into whole plants. (The phrase "immature gametic cell" (IGC) is applied here to gametes—megaspores and microspores alike, in the case of heterosporous plants—that have developed through the mitotic division of meiosis, i.e., a donor plant used in the present invention must support gametic development at least to the first-mitosis stage.) In those instances where, as in somatic hybridization, two "parent" plants are employed to produce a phenotypically-sterile variant which is to be the source for IGCs, at least one, and preferably both, of the parent plants should yield IGCs that can be cultured and regenerated into whole plants. Among the crops currently regenerable from IGCs, preferably microspores, are barley, wheat, corn, sunflower, datura, sweet pepper, alfalfa, tobacco, rice, muskmelon, petunia, triticale, rapeseed and other members of Brassica, potato, tomato, barley, millet, coconut, onion, coffee, soybeans, Aesculus, Populus, Hevea and Orchidaceae. In species where the generation time runs into years, as it does for trees and orchids, the time-saving advantages of the present invention are particularly evident.

Microspores for use according to the present invention are preferably obtained by homogenizing whole flower buds at high speed, in a microblender of the type Micro S/S sold by Eberback Co. (Ann Arbor, Mich.), which microblender contains cool (about 12° C.) wash medium (hormone-free B5, according to Gamburg et al, *Exp. Cell Res.* 50: 151–58 (1968)). See Swanson et al, *Plant Cell Rep.* 6: 94–97 (1987), the contents of which are hereby incorporated by references. Filtering of the homogenate yields large numbers of microspores, free of tissue and cellular debris.

Between 700 and 1,000 embryos per bud can be obtained routinely by this approach, with comparable yields and quality of microspores as have been reported for anther culture. The latter can also be used in the present invention as a source for microspores, in accordance with the disclosures of Chuong and Beversdorf, *Plant Sci.* 39: 219–26 (1985), and Lichter, *Z. Pflanzenphysiol.* 103: 229 (1981), the respective contents of which are hereby incorporated by reference. More specifically, anthers obtained from flower buds of plants grown from seed are macerated in a washing solution of B5 or other known medium, and the resulting suspension is aseptically filtered to obtain microspores.

It is especially preferred that the resulting isolated microspores be incubated over night, at about 30° C., in a modified Lichter medium (microspore medium), see Lichter, *Z. Flanzenphysiol.* 105: 427–434 (1982), containing 13 wt.% sucrose but no potato extract or hormones. After incubation, the microspores are centrifuged and resuspended in fresh microspore medium before being plated, typically in conventional petri dishes. Initiation of successful microspore culture, characterized by an increase in microspore volume, usually occurs within 24 hours at around 30° C. After about 5–7 days, cell clusters with well-defined epidermal layers (proembryos) are observed in culture, followed by the observation of typically heart-shaped or torpedo-shaped embryos within approximately 12 to 14 days. It is particularly preferred that the microspore cultures are maintained in darkness during this period. It is also preferred that, after about two weeks in culture, the embryos are subjected to mild shaking, which has been found to improve quality (percentage of torpedo-shaped embryos), synchrony and speed of embryo development.

After some three to four weeks in culture, torpedo-shaped embryos are transferred to a basal solid B5 medium with no hormones and 2% sucrose. Plant regeneration will occur directly from approximately 5 to 20% of these embryos, with later embryo development occurring upon subsequent subcultures. Alternatively, plant regeneration can be accomplished directly by placing the embryos, radicle downward through a filter paper interface, into Pro Mix which has been dampened with water. This "nursery" arrangement is maintained aseptically, e.g., in 100×25-mm deep petri dishes; the final moisture level should be approximately 15 mls of water per petri dish. The dish is placed in the light at approximately 250 $\mu E \cdot m^{-2} \cdot s^{-1}$ at 20–25° C. This procedure has produced as high as 90% direct plant regeneration from the embryos in 7 to 10 days. When proper torpedo-stage embryos are used, the initial shoots appear from the apical meristem, as is desired.

Regenerable megaspores can be obtained from the ovules, ovaries or even larger pieces of inflorescence of a functionally-sterile plant variant, by culturing these tissues on a synthetic solid or liquid medium, which may be the same as the anther-culture medium. Haploid plants can then be obtained by the parthenogenic development of a megaspore into an embryo. This technique has proved successful in monocotyledons, as disclosed, e.g., by Kott and Kasha in CEREAL TISSUE AND CELL CULTURE, Chapter 2 (Martinus Nijhoff/Dr. W. Junk Publ. 1985); in dicotyledons, see Geyt et al, *Theor Appl. Genet.* 73: 920–25 (1985); and in gymnosperms, see Rohr in CELL AND TISSUE CULTURE IN FORESTRY (Martinus Nijhoff Publ. 1987).

As was indicated previously, any procedure by which a phenotypically-sterile plant is produced can be readily modified, pursuant to the present invention, to incorporate the steps of generating embryos from IGCs of the donor plant and, thereafter, determining which embryos yield fertile plants. Thus, a procedure that entails isolation of a desired variant from tissue culture, for example, with the application of selective growth conditions in vitro as disclosed in U.S. Pat. No. 4,443,971, the contents of which are hereby incorporated by reference, and/or with the treatment of cultured cells with a mutagenic agent, can be augmented in accordance with the present invention to include obtaining IGCs from an isolated variant that is functionally sterile, culturing the IGCs to obtain of population of embryos, and then screening the IGC-derived embryos to identify those that provide fertile plants.

In analogous fashion, a phenotypically-sterile variant which is the product of plant transformation, e.g., following the disclosure of U.S. Pat. No. 4,684,611 or U.S. Pat. No. 4,693,976, the respective contents of which are hereby incorporated by reference; or of somatic or gametosomatic hybridization, see Pirrie and Power, *Theor. Appl. Genet.* 72: 48–52 (1986), and Hoffman and Adaihi, *Planta* 153: 586–93 (1981), can be the source of IGCs that are manipulated as described above to obtain plants having desirable identifying properties, but not the relative infertility, of the original variant. If a desired trait is selectable in vitro, an agent ("selection agent") which differentially influences the viability of cultured IGCs—for example, a herbicide or other cytotoxic chemical, or a hybridizing agent like cupferron or another substance that affects gametic development—can be added to the IGC culture medium, thereby to assure that only plants having the desired trait are regenerated.

Alternatively, the IGC-derived embryos (or cells obtained from embryonic tissue) can themselves be exposed to the selection agent. If cells are to be so treated, it is preferable that they be embryo-derived protoplasts, i.e., cells from which the pectocellulose cell walls have been removed, either by mechanical means or by enzymatic digestion as disclosed by Eriksson, "Protoplast Isolation and Culture," in PLANT PROTOPLASTS 1-20 (CRC Press 1983).

In this regard, the selection agent to which the cultured IGCs, IGC-derived embryos or embryonic cells are exposed, pursuant to the present invention, can be a host-specific toxin (HST) of the sort disclosed by Nishimura and Kohmoto, *Ann. Rev. Phytopathol.* 21: 87–116 (1983), thereby to select for resistance to the HST. For example, the saprophytic pathogen Alternaria, which is responsible for disease in many plants, produces an HST, tolerance to which has been correlated with disease resistance in several plant species.

In particular, rapeseed (*Brassica napus*) is susceptible to the disease caused by (and, apparently, to the HST of) the pathogen *Alternaria brassicae*. The HST of *A. brassicae* has been isolated and characterized as described, e.g., by Ayer and Pena-Rodrigues, *J. Nat. Products* 50: 400–17 (1987), the contents of which are hereby incorporated by reference. In contrast, white mustard (*B. hirta*; also known as *Sinapsis alba*) is resistant to the black-spot disease caused by *A. brassicae*.

Although *B. napus* and *B. hirta* are sexually incompatible, the two species could be hybridized somatically, via protoplast fusion as described above, to obtain phenotypically-sterile plants that would serve as donors for IGCs (preferably, microspores) in the present invention. For example, *B. napus* and *B. hirta* protoplasts can be fused and subsequently treated with *A. brassicae* HST to eliminate *B. napus* homokaryons. (As an optional pretreatment, the *B. hirta* protoplasts can be exposed to an agent, such as gamma irradiation (causing chromosomal breakages) or iodoacetamide (inhibiting metabolism), that prevents the treated protoplasts from developing into plants.) The surviving *B. napus/B. hirta* fusion products can then be regenerated to obtain the donor plants for use in the present invention. To ensure that the IGC segregants from the donor hybrid carry the essential elements for Alternaria tolerance, the IGCs can be treated with *A. brassicae* HST in culture.

Where one is attempting to produce a fertile, interspecific or intergeneric plant variant, as in the preceding example of somatic hybridization in Brassica, there may well be insufficient chromosomal homology to permit direct recombination ("crossing-over") of genetic material from the respective parent species. In such instances, achieving fertility in the variant may require chromosomal breakage and subsequent exchange ("translocation") of relatively small chromosome fragments during mitosis, thereby to obtain the proper combination, in individual cells of the segregating IGC population, for both fertility and the desired parental characteristics.

In one preferred embodiment of the present invention, therefore, the buds or premitotic gametic cells of the IGC-donor plant are treated with a mutagenic agent, such as gamma, X-ray or ultraviolet irradiation, in order to promote chromosomal breakage and, hence, translocation events which would be reflected in certain IGC-derived embryos that were developable into fertile plants displaying a desirable trait of the respective parent species. Alternatively, the IGCs can themselves be subjected to treatment in vitro with the mutagenic agent, thereby to induce chromosomal fragmentation and, during a subsequent mitosis, segregation of the fragment(s) in a desirable configuration. In another preferred embodiment, the donor plant is a somatic hybrid of two parent plants, at least one of which was subjected to a mutagenizing treatment prior to somatic fusion.

The screening step of the present invention can be effected by growing mature plants out of plantlets that are developed, via conventional techniques, from embryos derived from IGCs of the functionally-sterile donor plant. Those mature plants that are fertile can then be identified visually by reference to gross morphological indicators of normality, like anther development and flower structure, or by and seed set. In addition, further understanding of the genetic causes of sterility should make in vitro detection of sterile phenotypes feasible. Approaches to this end could include the use of restriction-fragment length polymorphisms (RFLPs); the rapid determination of DNA levels, e.g. in determining polyploidy and aneuploidy, via methods such as cell-sorting; and the detection of specific genes or gene products which affect fertility.

Those plants generated from IGCs that are not spontaneously doubled-haploids and, hence, may be sterile for that reason alone can be treated with colchicine in accordance with conventional methodology, see, e.g., Chuong and Beversdorf, *Plant Sci.* 39: 219-26 (1985), and then tested for fertility. In a population of plants generated from IGCs, the incidence of spontaneously doubled plants is generally expected to range between about 5% and 20%, although the range may be affected by the genetic composition of the donor plants and by alterations to the standard medium or culture conditions.

The present invention is further described by reference to the following, illustrative example.

EXAMPLE

Recovering Fertile Plant Material From A Phenotypically-Sterile Variant Produced From Cells (Protoplasts) Obtained From IGC-Derived Embryos.

PRODUCTION OF A HERBICIDE-TOLERANT, PHENOTYPICALLY-STERILE MUTANT: *Brassica napus* L. (cv. "Topas") plants were grown in Pro Mix-C (Plant Products, Toronto, Canada) in 8-inch fiber pots. A 16-hour photoperiod of at least 400 $\mu$E $m^{-2} \cdot s^{-1}$ at 18° C. was used with an 8-hour dark interval at 13° C. Fertilizer 20-10-20 (N:P:K) was applied with routine watering (3 to 4 times per week) once plants were past the three-leaf stage.

Young flower buds (0.5 to 5.0 mm in size) from the upper racemes of the *B. Napus* plants were surface sterilized for 15 minutes in 5% sodium hypochlorite and given three five-minute rinses in sterile distilled water. The buds were placed in a cool (refrigerated) microblender (Micro S/S Eberbach Co.) containing cool (12° C.) hormone-free B5 wash medium (4 ml for every 10 buds) with 13% sucrose and blended at high speed for 6 to 7 seconds. The slurries from these treatments were passed through two layers of Nitex (pore size 48 $\mu$m, product of B.SH. Thompson Co., Toronto) and collected in centrifuge tubes. The blender and Nitex were then rinsed with B5 wash medium; the filtrates were centrifuged at 350 g for ten minutes and the supernatant discarded. The pellet was resuspended in B5 wash and recentrifuged for two additional washes.

The resulting microspores were suspended in B5 medium and incubated overnight at 30° C. The microspores were then recentrifuged and resuspended in fresh medium, where normal embryogenesis was observed. Three weeks after microspore isolation, the microspore-derived embryos were transferred from liquid medium to solid B5 medium (without hormones) and, after two more weeks, to solid MS medium (pH 6) supplemented with the auxin 2,4-dichlorophenoxyacetic acid (0.01 mg/1) and kinetin (0.05 mg/1). In the presence of these hormones, the cultured embryos became enlarged, and formation of secondary embryos was observed.

Protoplasts were then isolated from the enlarged embryos via a protocol similar to that of Barsby et al, *Plant Cell Rep.*: 5: 101-03 (1986), the contents of which are hereby incorporated by reference. The basic protocol entails cell-wall digestion in an enzymatic solution of 1.0% cellulase R-10 and 0.1% Macerozyme R-10. After filtration the protoplasts are rinsed and collected by flotation. The protoplasts are suspended at approximately 100,000 protoplasts/ml in the protoplast culture medium and then placed in Quadrant plates, with the protoplast culture medium in contact with the reservoir medium, as described by Shepard et al, *Science* 208: 17 (1980). Modifications to this protoplast isolation method included the removal of casein hydrolysate from the protoplast medium, and the addition 0.75 parts per billion (ppb) of a sulfonylurea herbicide, chlorsulfuron, to the protoplast medium but not to the reservoir medium.

Under these culture conditions, one callus colony survived and was unaffected by transferal to dilution medium containing 2.5 ppb chlorsulfuron. By contrast, Topas protoplasts were killed in the presence of only 0.35 ppb chlorsulfuron, when the herbicide was added to both the reservoir medium and the protoplast medium.

Shoot regeneration was induced by transferring the surviving colony to MS medium containing 1% sucrose, 100 mg/1 casein hydrolysate, 2 mg/1 kinetin, 2 mg/1 zeatin and 0.01 mg/1 IAA ("regeneration medium"). After 14 days at 25° C. (16-hour photoperiod of 100 $\mu$E$\cdot$m$^{-2}\cdot$s$^{-1}$), the resulting nodular colony was transferred to fresh regeneration medium, and a shoot developed. Shoot tissue continued to grow when it was cultured in hormone-free B5 medium containing 0.45% agarose (Type 1, Sigma) and 2% sucrose.

Plantlets developed within 3 to 6 weeks. Nodal explants of this plant were maintained and increased by transferring 1- to 3-cm nodal sectors to B5 medium, and were subsequently transferred to Pro Mix. The plants thus obtained were sprayed at the 3-5 leaf stage with chlorsulfuron (post-emergent) in a spray chamber (Research Instruments, Guelph, Ontario, Canada). The chamber contained a boom sprayer with a flat fan nozzle (TeeJet SS8002), and was calibrated to deliver 0, 0.5, 20 and 40 grams per hectare (g/ha) of chlorsulfuron, respectively, with 0.15% Agral 90 as a surfactant. Four plants of each line were used per treatment.

The mutant plants were found to be approximately an order of magnitude more tolerant to chlorsulfuron than the parental plants. The mutant plants were aneuploid (chromosome number of pollen mother cells was 26-29), and functionally sterile relative to the norm for *B. napus*, i.e., they produced no seed when self-fertilized or when reciprocally crossed to wild type plants. Approximately 100 plants propagated from nodal explants or form cuttings of the mutant were subjected to extensive selfing; these plants produced in excess of 20,000 flowers of which several hundred were manually selfed. These exhaustive efforts produced a few seeds (S1), with an average of less than one seed per plant.

The seeds were planted in Metro Mix which had been sprayed with up to 25 g/ha of chlorsulfuron, five days prior to sowing (pre-plant incorporated). Thirty S1 plants were examined and found to be both chlorsulfuron-tolerant and functionally sterile. Reciprocal crosses of the mutant plants with wild-type plants also produced a few seeds (less than 1% produced a seed-bearing pod which contained a single seed). By contrast, more than 90% of wild-type crosses produced seed, with approximately 15-20 seeds per pod. Of the 15 F1 hybrid seeds tested, all were chlorsulfuron-tolerant and functionally sterile, although the plant morphology of some of the hybrids was improved.

PRODUCTION OF FERTILE PLANTS VIA THE PRESENT INVENTION: Microspores were isolated in the above-described manner from one of the asexually-propagated mutant plants, and these IGCs were cultured in the presence of 10 ppb chlorsulfuron, providing some 1050 embryos. One hundred of these embryos were selected at random and developed into whole plants ("regenerants") via the micropropagation method described above. Among the regenerants, five plants produced more than 100 seeds per plant when self-fertilized, respectively, reflecting a 260-to-1800% increase in fertility over the original mutant (see Table 1). The remaining regenerants were functionally sterile, and varied in morphology from grossly abnormal (dwarfs, semidwarfs, plants with few or no flowers, some very large plants, some plants with haploid-like but still abnormal phenotypes), to plants of fairly normal appearance. All fertile plants were of normal appearance for B. napus.

The five self-fertile regenerants were considered spontaneous doubled haploids, i.e., no colchicine had been used during embryogenesis. Tests for activity of the enzyme acetolacetate synthase (ALS), which is the target of sulfonylurea herbicides like chlorsulfuron as well as of imididazolinones, showed that the regenerants possessed activity comparable to that of the parent (Topas) of the IGC-donor plant. This result indicated that the molecular components of the enzyme had not been altered in the mutants, i.e., the regenerants possessed an enzyme ("parental-type" ALS) like that characteristic of Topas.

At least one of the regenerants was found, upon standard cytological examination, to be euploid (chromosome number: 19). Reciprocal cross-pollination of that plant with wild-type stock (cv. Topas) yielded progeny characterized by normal seed set.

TABLE 1

Relative Morphological and Fertility Characteristics of Chlorsulfuron-Tolerant Brassica Mutant and Selected IGC-Derived Regenerants Thereof.

| Genotype | Seed Set[1] | Chlorsulfuron Tolerance[2] | Relative Fertility[3] |
|---|---|---|---|
| Topas (wild type) | 1500 | 0.5 | — |
| Mutant | 0.5 | 40 | nil |
| Regenerants | | | |
| M15 | 155 | 25+* | 310 fold |
| M25 | 900 | 25+ | 1800 fold |
| M26 | 300 | 25+ | 600 fold |
| M29 | 130 | 25+ | 260 fold |
| M44 | 160 | 25+ | 320 fold |

[1] Seeds were produced via self-fertilization and were harvested five weeks post-anthesis.
[2] Tolerance to chlorsulfuron was determined by planting selfed seed in Metro Mix that had been treated with 0, 0.5, 1, 10, 25, and 40 g/ha (PPI), as outlined above. The numbers reported in Table 1 represent the highest level of chlorsulfuron tolerated (g/ha) before plant death, and in the case of the regenerates represents the highest level tested.
[3] "Relative fertility" is reported as the change in seed set compared to mutant from which IGCs were obtained.
*The highest concentration of chlorsulfuron tested with the regenerants was 25 g/ha.

What is claimed is:

1. A process for creating a plant having improved fertility, comprising:
   producing a culture of microspores obtained from a donor plant of the genus Brassica that has a seed yield of less than 50% of the wild type of the donor plant species;
   generating a plurality of plant embryos from cells in said culture;
   regenerating said embryos into whole plants; and
   selecting plants regenerated from said embryos which have improved fertility.

2. The process of claim 1, wherein said donor plant has a seed yield of less than 10% of the wild type.

3. The process of claim 1, wherein said donor plant has a seed yield of less than 1% of the wild type.

4. A process as claimed in claim 1, wherein said donor plant is a somatic hybrid.

5. A process as claimed in claim 1, wherein said donor plant is a sexual hybrid.

6. A process as claimed in claim 1, wherein said donor plant is a transgenic plant.

7. A process as claimed in claim 1, wherein said donor plant has been regenerated from cell culture.

8. A process as claimed in claim 7, wherein said donor plant is produced by a process comprising the step of exposing plant cells in culture to selective growth conditions.

9. A process as claimed in claim 1, further comprising the step of exposing said microspores, or said plant embryos, to a selection agent that has a selective effect on the viability of microspores or plant embryos, such that certain but not all of the exposed microspores or embryos are viable.

10. A process as claimed in claim 9, wherein said selection agent is one selected from the group consisting of a cytotoxic chemical, a substance affecting gametic development, or a host-specific toxin.

11. A process as claimed in claim 10, wherein said selection agent is a host-specific toxin produced by *Alternaria brassicae*.

12. A process as claimed in claim 1 wherein said microspores are obtained from a plant in which buds or premitotic gametic cells have been exposed to a mutagenic agent prior to producing said microspores.

13. A process as claimed in claim 1, wherein said donor plant is a somatic hybrid of two parent plants, at least one of which is exposed to mutagenic agent prior to somatic hybridization.

* * * * *